US007909767B2

(12) United States Patent
Li et al.

(10) Patent No.: US 7,909,767 B2
(45) Date of Patent: Mar. 22, 2011

(54) METHOD FOR MINIMIZING TRACKING SYSTEM INTERFERENCE

(75) Inventors: Dun Alex Li, Salem, NH (US); Nora T. Tgavalekos, Tewksbury, MA (US); Jonathan David Schiff, Andover, MA (US)

(73) Assignee: General Electric Company, Schenectady, NY (US)

( * ) Notice: Subject to any disclaimer, the term of this patent is extended or adjusted under 35 U.S.C. 154(b) by 765 days.

(21) Appl. No.: 11/866,865

(22) Filed: Oct. 3, 2007

(65) Prior Publication Data

US 2008/0287802 A1 Nov. 20, 2008

Related U.S. Application Data

(60) Provisional application No. 60/938,397, filed on May 16, 2007.

(51) Int. Cl.
*A61B 8/14* (2006.01)
(52) U.S. Cl. .......................... 600/467; 600/462; 600/466
(58) Field of Classification Search .................. None
See application file for complete search history.

(56) References Cited

U.S. PATENT DOCUMENTS

| | | | |
|---|---|---|---|
| 5,630,417 A * | 5/1997 | Petersen et al. ............... 600/443 |
| 6,233,476 B1 | 5/2001 | Strommer et al. |
| 6,662,034 B2 | 12/2003 | Segner et al. |
| 6,669,635 B2 | 12/2003 | Kessman et al. |
| 6,711,215 B1 | 3/2004 | Tziony et al. |
| 6,716,166 B2 | 4/2004 | Govari |
| 6,773,402 B2 | 8/2004 | Govari et al. |
| 7,090,639 B2 | 8/2006 | Govari |
| 7,156,816 B2 | 1/2007 | Schwartz et al. |
| 2001/0031919 A1 | 10/2001 | Strommer et al. |
| 2002/0005719 A1 | 1/2002 | Gilboa et al. |
| 2002/0026118 A1 | 2/2002 | Govari |
| 2002/0042571 A1 | 4/2002 | Gilboa et al. |
| 2003/0013958 A1 | 1/2003 | Govari et al. |
| 2003/0074011 A1 | 4/2003 | Gilboa et al. |
| 2003/0208102 A1 | 11/2003 | Gilboa |

(Continued)

FOREIGN PATENT DOCUMENTS

EP 1057455 A2 12/2000

OTHER PUBLICATIONS

Proulx T.L. et al, "Advances in Catheter-Based Ultrasound Imaging", IEEE International Ultrasonics Symposium Proceedings, 2005.

(Continued)

*Primary Examiner* — Unsu Jung
*Assistant Examiner* — Nigel Fontenot
(74) *Attorney, Agent, or Firm* — Andrus, Sceales, Starke & Sawall, LLP

(57) ABSTRACT

A method for minimizing tracking system interference caused by a motor driven ultrasonic imaging device is disclosed herein. The method includes providing an ultrasonic imaging device adapted to obtain a generally real time three-dimensional image. The ultrasonic imaging device includes a motor configured to rotate a transducer array within a catheter housing. The method for minimizing tracking system interference also includes estimating a noise signal produced by the motor, selecting a tracking system signal strength and/or frequency adapted to minimize a tracking system interference, and implementing a field generator to produce a tracking system signal at the selected tracking system signal strength and/or frequency.

16 Claims, 4 Drawing Sheets

U.S. PATENT DOCUMENTS

| | | |
|---|---|---|
| 2003/0231789 A1 | 12/2003 | Willis et al. |
| 2004/0097805 A1 | 5/2004 | Verard et al. |
| 2004/0102769 A1 | 5/2004 | Schwartz et al. |
| 2004/0138548 A1 | 7/2004 | Strommer et al. |
| 2004/0162507 A1 | 8/2004 | Govari |
| 2004/0162550 A1 | 8/2004 | Govari et al. |
| 2004/0254458 A1 | 12/2004 | Govari |
| 2005/0033136 A1 | 2/2005 | Govari et al. |
| 2005/0197557 A1 | 9/2005 | Strommer et al. |
| 2006/0241445 A1 | 10/2006 | Altmann et al. |
| 2006/0253024 A1 | 11/2006 | Altmann et al. |
| 2006/0253029 A1 | 11/2006 | Altmann et al. |
| 2006/0253030 A1 | 11/2006 | Altmann et al. |
| 2006/0253031 A1 | 11/2006 | Altmann et al. |
| 2006/0253032 A1 | 11/2006 | Altmann et al. |
| 2007/0073135 A1 | 3/2007 | Lee et al. |
| 2007/0106147 A1 | 5/2007 | Altmann et al. |
| 2007/0167801 A1 | 7/2007 | Webler et al. |
| 2007/0167821 A1 | 7/2007 | Lee et al. |
| 2007/0225593 A1 | 9/2007 | Porath et al. |

OTHER PUBLICATIONS

Kanckstedt, et al., "Semi-automated 3-dimentional intracardiac echocardiography :development and initial clinical experience of a new system to guide ablation procedures", Hearth Rhythm, 3(12):1453-9, 2006.

Proulx, T.L. et al, "Advances in Catheter-Based Ultrasound Imaging", IEEE International Ultrasonics Symposium Proceedings, 2005.

Martin, R. et al, "A Miniature Position and Orientation Locator for Three Dimensional Echocardiography", IEEE Proceedings on Computer in Cardiology, pp. 25-28, 1993.

Beasley, R.A. et al, "Registration of ultrasound images", www.tgt.vanderbilt.edu/archive/Registration of ultrasound images.pdf, Medical Imaging 1999: Image Display, Proceedings of SPIE, pp. 3658125-3658132, 1999.

Rotger, D. et al, "Multimodal Registration of Intravascular Ultrasound and Angiography", Computer Vision Center Universitat Autonoma de Barcelona Bellaterra, Spain, www.cvc.uab.es/~petia/caseib2002.pdf, In Proceedings of the XX Congreso Annual de la Sociedad Espanola de Ingeniera Biomedica (CASEIB), 2002, pp. 137-140.

Huang, X. et al, "Dynamic 3D Ultrasound and MR Image Registration of the Beating Heart", MICCAI, LNCS 3750, pp. 171-178, 2005.

Leotta, D.F. et al., "Three Dimensional Ultrasound Imaging Using Multiple Magnetic Tracking Systems and Miniature Magnetic Sensors", IEEE on Ultrasonics Symposium, pp. 1415-1418, 1995.

Pagoulatos, N. et al., "Interactive 3-D Registration of Ultrasound and Magnetic Resonance Images Based on a Magnetic Position Sensor", IEEE on Info. Tech. In Biomedicine, vol. 3, No. 4, 1999, pp. 278-288.

USPTO Office Action mailed Sep. 13, 2010—U.S. Appl. No. 11/863,656, filed Sep. 28, 2007.

* cited by examiner

METHOD FOR MINIMIZING TRACKING
SYSTEM INTERFERENCE

RELATED APPLICATIONS

This application claims priority to Provisional Application No. 60/938,397 filed on May 16, 2007, and is hereby incorporated herein by reference in its entirety.

BACKGROUND OF THE INVENTION

The subject matter disclosed herein relates to a method for minimizing tracking system interference.

Atrial fibrillation is characterized by very rapid uncoordinated electrical signals in the atria of the heart resulting in a rapid and irregular heart-beat. Atrial fibrillation can significantly impact a patient's quality of life producing symptoms such as shortness of breath, weakness, difficulty exercising, sweating, dizziness, and fainting. In some patients, atrial fibrillation can be associated with increased risk of stroke, heart failure, or heart muscle disease. It is known to treat atrial fibrillation using a process referred to as cardiac ablation wherein a small section of heart tissue is killed or otherwise rendered inactive thereby breaking the electrical pathways causing the fibrillation.

The performance of interventional procedures such as cardiac ablation can be facilitated by systems adapted to visualize cardiac anatomy in real-time. Exemplary real-time visualization systems include intracardiac echocardiography (ICE) systems incorporating a rotatable transducer array driven by an ICE motor and disposed within an ICE catheter. One problem with the implementation of an ICE system for the performance of interventional procedures is that electromagnetic (EM) tracking systems implemented to track the ICE catheter and/or other interventional devices may be rendered imprecise by interference from the ICE motor.

BRIEF DESCRIPTION OF THE INVENTION

The above-mentioned shortcomings, disadvantages and problems are addressed herein which will be understood by reading and understanding the following specification.

In an embodiment, a method for minimizing tracking system interference caused by a motor driven ultrasonic imaging device includes providing an ultrasonic imaging device adapted to obtain a generally real time three-dimensional image. The ultrasonic imaging device includes a motor configured to rotate a transducer array within a catheter housing. The method for minimizing tracking system interference also includes estimating a noise signal produced by the motor, selecting a tracking system signal strength and/or frequency adapted to minimize a tracking system interference, and implementing a field generator to produce a tracking system signal at the selected tracking system signal strength and/or frequency.

In another embodiment, a method for minimizing tracking system interference caused by a motor driven ultrasonic imaging device includes providing an ultrasonic imaging device adapted to obtain a generally real time three-dimensional image. The ultrasonic imaging device includes a motor configured to rotate a transducer array within a catheter housing. The method for minimizing tracking system interference also includes providing a field sensor disposed within the catheter housing, estimating a noise signal produced by the motor, and removing the noise signal from a composite signal recorded by the field sensor.

In another embodiment, a method for minimizing tracking system interference caused by a motor driven ultrasonic imaging device includes providing an ultrasonic imaging device adapted to obtain a generally real time three-dimensional image. The ultrasonic imaging device includes a motor configured to rotate a transducer array within a catheter housing. The method for minimizing tracking system interference also includes providing a tracking system operatively connected to the catheter housing, and coordinating the operation of the motor and the tracking system. The coordination of the motor and the tracking system includes operating the motor in a manner adapted to minimize a noise signal produced by the motor; and implementing the tracking system to estimate the position and/or orientation of the catheter housing exclusively during periods wherein the motor is being operated in a manner adapted to minimize the noise signal.

Various other features, objects, and advantages of the invention will be made apparent to those skilled in the art from the accompanying drawings and detailed description thereof.

DETAILED DESCRIPTION OF THE INVENTION

In the following detailed description, reference is made to the accompanying drawings that form a part hereof, and in which is shown by way of illustration specific embodiments that may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken as limiting the scope of the invention.

Figure 1:
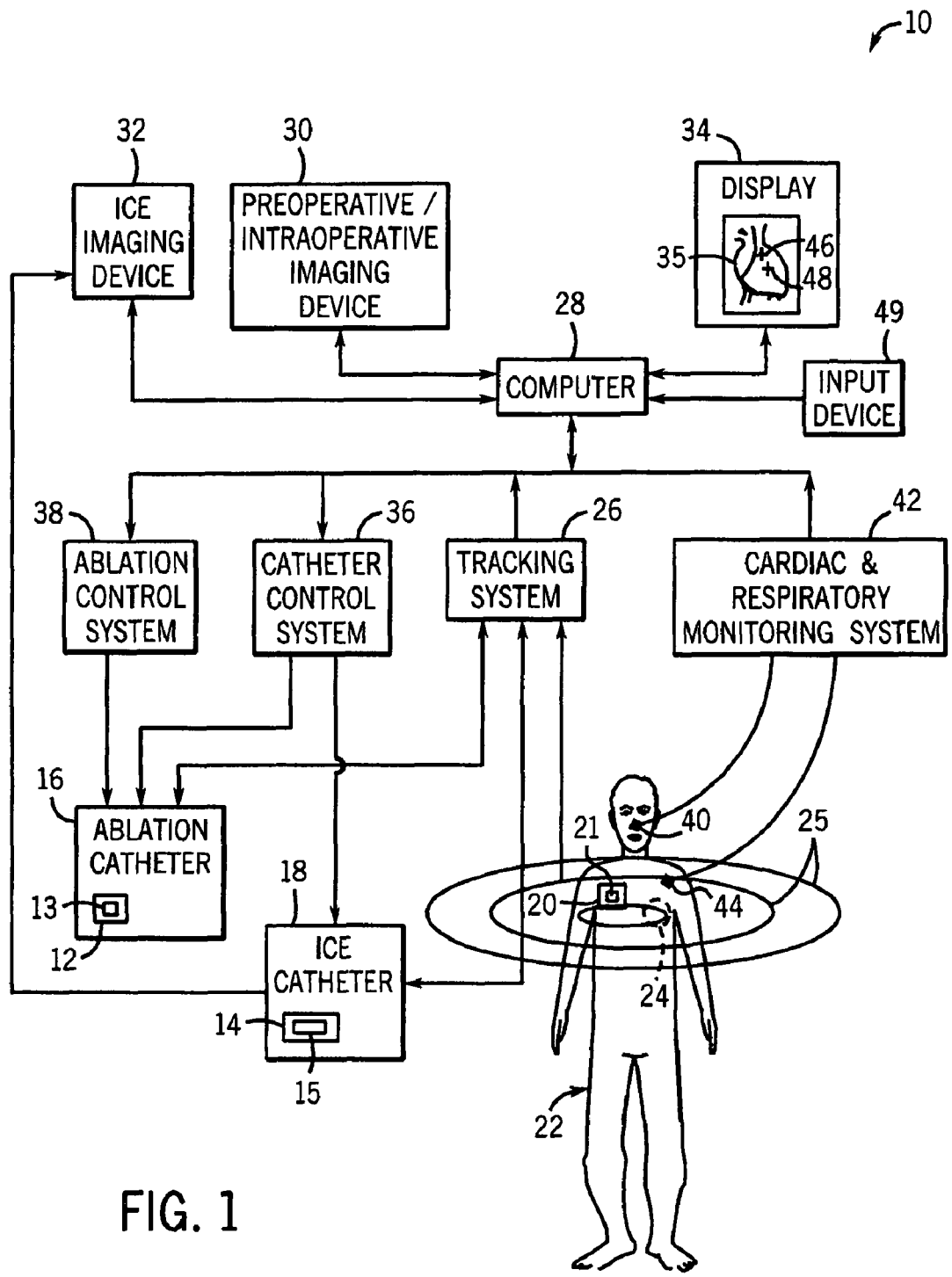
FIG. 1 is a schematic representation of an imaging and navigation system in accordance with an embodiment.

Referring to FIG. 1, a system 10 is shown in accordance with one embodiment. The system 10 will hereinafter be described as an imaging and navigation system adapted for treating atrial fibrillation using an ablation procedure. The system 10 will also hereinafter be described as implementing intracardiac echocardiography (ICE) to facilitate the performance of the ablation procedure. It should, however, be appreciated that the system 10 may also be implemented to treat other medical conditions and to perform other procedures, and that the system 10 may implement alternate ultrasonic technologies in place of ICE.

The navigation portion of the imaging and navigation system 10 includes a tracking system 26 that is operatively connected to a plurality of tracking elements 12, 14 and 20. According to one embodiment, the tracking system 26 and tracking elements 12, 14 and 20 implement electromagnetic (EM) tracking technology, however, alternate tracking technologies and/or tracking systems may be envisioned. The tracking element 12 is adapted for attachment to an ablation catheter 16, and the tracking element 14 is adapted for attachment to an ICE catheter 18. For purposes of this disclosure, a catheter is defined to include any flexible medical delivery system such as, for example, an endoscope. The tracking element 20 can be rigidly attached to an internal organ (e.g., the heart 24) or to the external body of the patient 22 in a conventional manner. A tracking element 20 secured to the patient's heart 24 may be referred to as a "dynamic reference" because it is adapted to move along with the heart 24. An exemplary method of attaching the tracking element 20 to the patient's heart 24 is through a minimally invasive procedure using a dynamic reference catheter (not shown).

The present invention will hereinafter be described in accordance with an embodiment wherein the tracking element 20 comprises one or more field generators 21, the tracking element 12 comprises one or more field sensors 13, and the tracking element 14 comprises one or more field sensors 15. It should, however, be appreciated that according to alternate embodiments the tracking element 20 may include one or more field sensors and the tracking elements 12, 14 may each include one or more field generators. The field generator 21 generates a magnetic field 25 in an area that includes the target site (e.g., the patient's heart 24). The field sensors 13, 15 are adapted to measure the magnetic field 25, and to transmit the magnetic field measurements to the tracking system 26. The tracking system 26 implements the magnetic field measurements to calculate the position and orientation of the tracking elements 12, 14. After calculating the position and orientation of the tracking elements 12, 14, the position and orientation of the ablation catheter 16 and the ICE catheter 18 respectively attached thereto can also be calculated in a known manner.

The tracking system 26 transmits the catheter position and orientation data to a computer 28. The computer 28 registers the position and orientation data to an image obtained from a preoperative/intraoperative imaging device 30 and/or to an image obtained from an ICE imaging device 32. The preoperative/intraoperative imaging system 30 may, for example, include a CT imaging device, a MR imaging device, a PET imaging device, an ultrasound imaging device, an X-ray imaging device, or any other known imaging device, as well as any combinations thereof. The preoperative/intraoperative imaging device 30 may provide 2D, 3D or 4D images. For purposes of this disclosure, 4D refers to the three primary dimensions (i.e., as measured along X, Y and Z axes) and the fourth dimension which is time. Therefore, for purposes of this disclosure, 4D is synonymous with generally real time 3D. The ICE imaging device 32 is configured to obtain imaging data from the ICE catheter 18 and produce 2D, 3D or 4D images as will be described in detail hereinafter.

The catheter position and orientation data can be visualized on the display 34. According to one embodiment, graphic representations corresponding to the ablation catheter 16 and the ICE catheter 18 may be virtually superimposed on a patient image 35. In the embodiment of FIG. 1, the graphic representations corresponding to the catheters 16, 18 include the cross-hairs 46, 48 respectively representing the distal end portions of the ablation catheter 16 and the ICE catheter 18, however other embodiments may include a more complete rendering showing the catheters 16, 18 in detail. In a non-limiting manner, the patient image 35 may include a CT image, a MR image, a PET image, an ultrasound image or an X-ray image from the preoperative/intraoperative imaging device 30. The patient image 35 may also include a real time 3D image from the ICE imaging device 32, or a fused image comprising a plurality of images from the preoperative/intraoperative imaging device 30 and/or the ICE imaging device 32 that have been combined in a known manner.

The input device 49 may include any known apparatus or system such as a keyboard, mouse, touch screen, joystick, etc., and is generally adapted to allow a user to manually input data into the system 10. Although shown in FIG. 1 as a separate component, the input device 49 may alternatively be incorporated into one of the other system 10 components such as the computer 28 or the display 34. As an example, the input device 49 may include a touch screen device integrated into the design of the display 34 and adapted to facilitate surgical planning.

A catheter control system 36 is operatively connected to both the ablation catheter 16 and the ICE catheter 18. The catheter control system 36 is adapted to translate and steer the catheters 16, 18 through the patient 22 to a predefined destination at or near the patient's heart 24. The catheter control system 36 may be configured to translate and steer the catheters 16, 18 in response to manual operator inputs, or may be configured to automatically direct the catheters 16, 18 to a selectable target site. The catheter control system 36 may also be operatively connected to and configured to control a dynamic reference catheter (not shown) adapted to facilitate the attachment of the tracking element 20 to the patient's heart 24.

An ablation control system 38 controls the energy transfer to the ablation catheter 16. Accordingly, when an operator determines that the distal end of the ablation catheter 16 is in sufficiently close proximity to a targeted cardiac region, the ablation control system 38 can be implemented to transmit a selectable amount of energy. The transmission of energy in this manner kills or otherwise renders inactive the targeted region in order to break electrical pathways causing atrial fibrillation. In a non-limiting manner, the ablation control system 38 may implement radio frequency (RF), cryogenic, ultrasound, or laser technologies.

One or more respiratory sensors 40 can be positioned near the patient's mouth and/or nose in order to monitor respiration, and one or more cardiac sensors 44 can be positioned near the patient's heart 24 to monitor cardiac activity. The respiratory sensors 40 and the cardiac sensors 44 are operatively associated with and adapted to transmit sensor data to a monitoring system 42. Any sensor data collected by the monitoring system 42 is transferable to the computer 28 such that the computer 28 may be implemented to synchronize the operation of the tracking system 26, the imaging device 30, and/or the imaging device 32 with the patient's cardiac and respiratory activity. According to one example, the computer 28 may implement monitor data from the monitoring system 42 to acquire images during predefined portions of a patient's cardiac or respiratory cycle. According to another example, the computer 28 may implement data from the monitoring system 42 to sequence a series of 2D images or slices in a manner that corresponds with a patient's cardiac or respiratory cycle in order to provide a generally real time rendering of a dynamic object such as the patient's heart 24.

Figure 2:
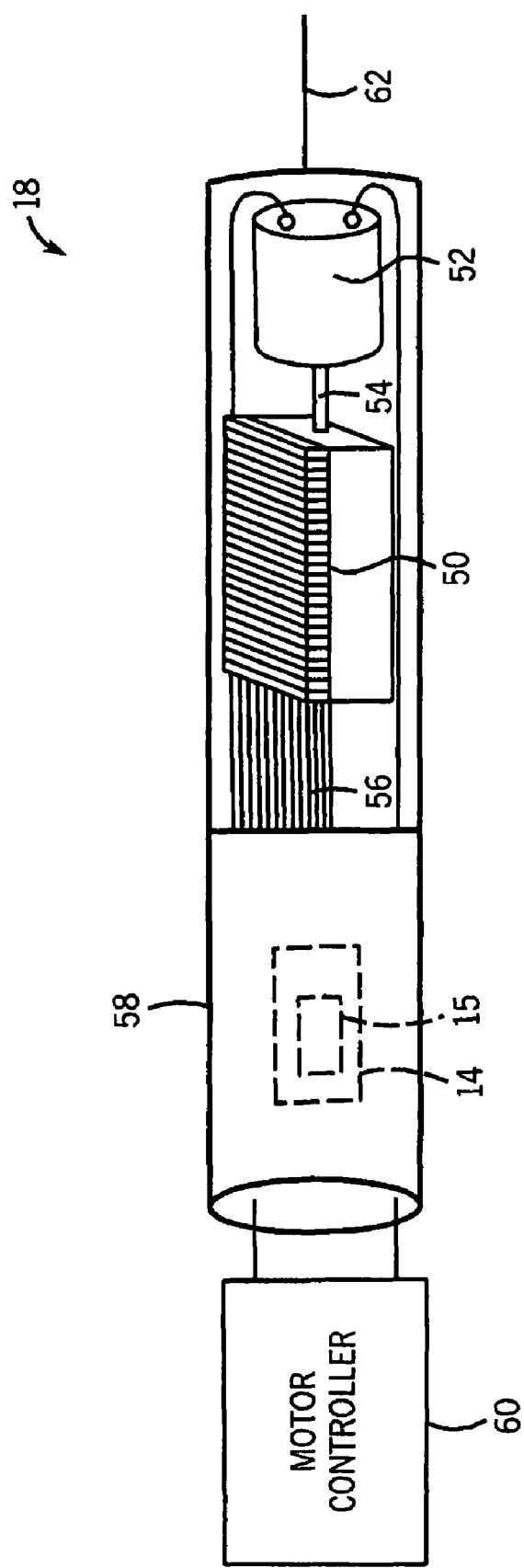
FIG. 2 is a partially cutaway schematic illustration of an ICE catheter in accordance with an embodiment.

Referring to FIG. 2, a more detailed illustration of the ICE catheter 18 is shown. The ICE catheter 18 will hereinafter be described in detail in accordance with an embodiment. It should, however, be appreciated that the ICE catheter 18 may be replaced with a similar catheter system adapted to retain any known ultrasonic imaging device.

The ICE catheter 18 comprises a transducer array 50, a motor 52, which may be internal or external to the space-critical environment, a drive shaft 54 or other mechanical connections between motor 52 and the transducer array 50, and an interconnect 56. The ICE catheter 18 further includes a catheter housing 58 enclosing the transducer array 50, motor 52, interconnect 56 and drive shaft 54. In the depicted embodiment, the transducer array 50 is mounted on drive shaft 54 and the transducer array 50 is rotatable with the drive shaft 54. The rotational motion of the transducer array 50 is controlled by motor controller 60 and motor 52. Interconnect 56 refers to, for example, cables and other connections coupling the transducer array 50 with the ICE imaging device 32 (shown in FIG. 1) for use in receiving and/or transmitting signals therebetween. In an embodiment, interconnect 56 is configured to reduce its respective torque load on the transducer array 50 and motor 52. The catheter housing 58 is of a material, size and shape adaptable for internal imaging applications and insertion into regions of interest. According to the embodiment depicted in FIG. 2, the catheter housing 58 is generally cylindrical defining a longitudinal axis 62.

The catheter housing 58, or at least the portion that intersects the ultrasound imaging volume, is acoustically transparent, e.g. low attenuation and scattering, acoustic impedance near that of blood and tissue (Z~1.5M Rayl). The space between the transducer and the housing can be filled with an acoustic coupling fluid (not shown), e.g., water, with acoustic impedance and sound velocity near those of blood and tissue (Z~1.5 M Rayl, V~1540 m/sec).

According to one embodiment, the transducer array 50 is a 64-element one-dimensional array having 0.110 mm azimuth pitch, 2.5 mm elevation and 6.5 MHz center frequency. The elements of the transducer array 50 are electronically phased in order to acquire a sector image parallel to the longitudinal axis 62 of the catheter housing 58. The transducer array 50 is mechanically rotated about the longitudinal axis 62 to image a three-dimensional volume. The transducer array 50 captures a plurality of two-dimensional images as it is being rotated. The plurality of two-dimensional images are transmitted to the ICE imaging device 32 (shown in FIG. 1) which is configured to sequentially assemble the two-dimensional images in order to produce a three-dimensional image.

The rate at which the transducer array 50 is rotated about the longitudinal axis 62 can be regulated by the motor controller 60. The transducer array 50 can be rotated relatively slowly to produce a 3D image, or relatively quickly to produce a generally real time 3D image (i.e., a 4D image). The motor controller 60 is also operable to vary the direction of rotation to produce an oscillatory transducer array motion. In this manner, the range of motion and imaged volume are restricted such that the transducer array 50 can focus on imaging a specific region and can update the 3D image of that region more frequently, thereby providing a generally real time 3D, or 4D, image.

Referring to FIGS. 1 and 2, an embodiment of the ICE catheter 18 includes an integrally attached tracking element 14 disposed within the catheter housing 58. The integrally attached tracking element 14 is adapted to work in combination with the tracking element 20 and the tracking system 26 to estimate the position and/or orientation of the ICE catheter 18. As previously described, the tracking element 14 may comprise either the field sensor 15 or a field generator (not shown) similar to the field generator 21.

It should be appreciated by those skilled in the art that the previously described ICE catheter 18 is a single embodiment, and that alternate configurations may be envisioned. For example, the transducer array 50, motor 52 and drive shaft 54 define a mechanical 4D ICE embodiment that could be replaced by a functionally equivalent electrical 4D ICE embodiment (not shown). The electrical 4D ICE embodiment may, for example, comprise a 2D matrix transducer array (not shown) integrated with an electronic device (not shown) configured to steer the ultrasound beam in azimuth and elevation. In this manner, the electrical 4D ICE embodiment could image a 3D or 4D volume without necessarily moving the transducer array.

Figure 3:
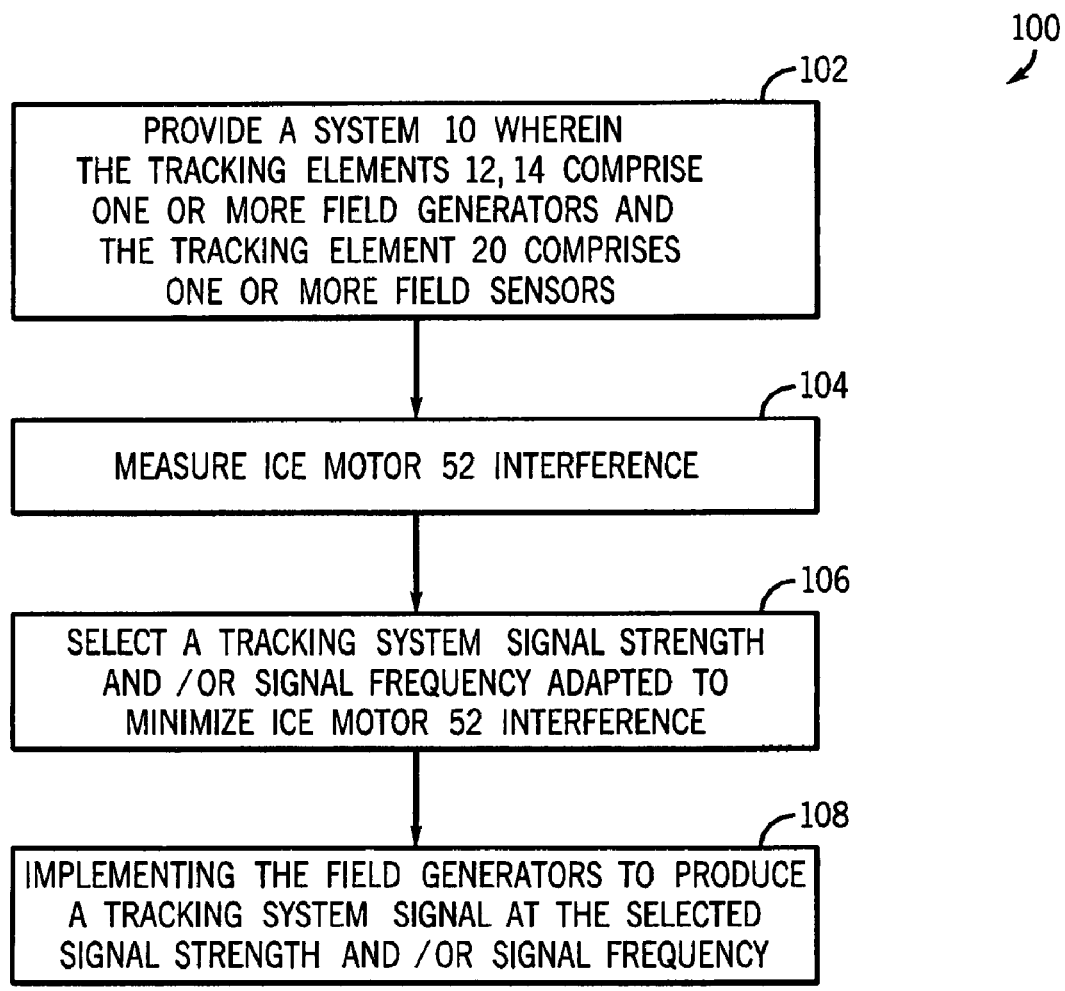
FIG. 3 is a flow chart illustrating a method in accordance with an embodiment.

Referring to FIG. 3, a block diagram illustrates a method 100 in accordance with an embodiment. The technical effect of the method 100 is to minimize tracking system interference. The individual blocks shown in FIG. 3 represent steps that may be performed in accordance with the method 100.

Referring to FIGS. 1 and 3, at step 102 of the method 100, a system 10 is provided wherein the tracking elements 12, 14 comprise one or more field generators similar to the field generator 21, and the tracking element 20 comprises one or more field sensors similar to the field sensors 13, 15. By configuring the system 10 in the manner described, the ICE motor 52 (shown in FIG. 2) is separated from the field sensors of the tracking element 20. As the ICE motor 52 is a potential source of tracking system interference, this separation minimizes the amount of interference recorded by the field sensors and thereby improves tracking system precision.

At step 104 interference from the ICE motor 52 (shown in FIG. 2) is measured or estimated. According to one embodiment, ICE motor interference can be measured by turning off the field generators of the tracking elements 12, 14 so that the signal recorded by the field sensor of the tracking element 20 is primarily derived from the ICE motor 52. Alternatively, the ICE motor interference measurements or estimates can be obtained in any known manner such as, for example, by implementing ICE motor manufacturing specifications or previously acquired test data. It should be appreciated that step 104 is an optional step adapted to facilitate the selection of a tracking system signal strength and/or signal frequency at step 106.

At step 106 a tracking system signal strength and/or signal frequency is selected to minimize the effects of interference from the ICE motor 52 (shown in FIG. 2). As is known to those skilled in the art, the field sensor of the tracking element 20 generally records a composite signal comprising both a tracking system signal from the field generators and a noise signal primarily attributable to interference from the ICE motor 52. By increasing the tracking system signal strength relative to that of the ICE motor interference signal, the signal-to-noise ratio (SNR) of the composite signal is increased. Increasing the SNR of the composite signal minimizes any adverse effects associated with noise such that tracking system precision is improved. Accordingly, the selection of a tracking system signal strength and/or signal frequency at step 106 comprises selecting a signal strength and/or signal frequency that is sufficiently large to minimize the effects of ICE motor interference.

According to an embodiment, at step 106 the selected tracking system signal strength may be at least 1,000 times greater than that of the ICE motor signal. Therefore, if the signal strength of the ICE motor as measured at step 104 ranges from 600 to 1,000 analog/digital (A/D) counts, a tracking system signal strength of approximately 1,000,000 A/D counts may be selected at step 106.

According to another embodiment, at step 106 the selected tracking system signal frequency may be at least 10 times greater than that of the ICE motor signal. Therefore, if the signal frequency of the ICE motor as measured at step 104 is 300 hertz (Hz), a tracking system signal frequency of approximately 3 kilohertz (kHz) may be selected at step 106.

At step 108 the tracking element 14 field generators are implemented to produce the tracking system signal strength and/or signal frequency selected at step 106. More precisely, the tracking element 14 field generators are driven in a manner adapted to produce the selected tracking system signal strength and/or frequency of step 106. In this manner, the tracking system signal produced by the field generators of the ICE catheter 18 can minimize the effects of ICE motor interference and thereby improve tracking system precision. A similarly high strength/high frequency tracking system signal can be produced by the field generators of the ablation catheter 16 in order to minimize the effects of ICE motor interference when the catheters 16, 18 come into close proximity with each other.

Figure 4:
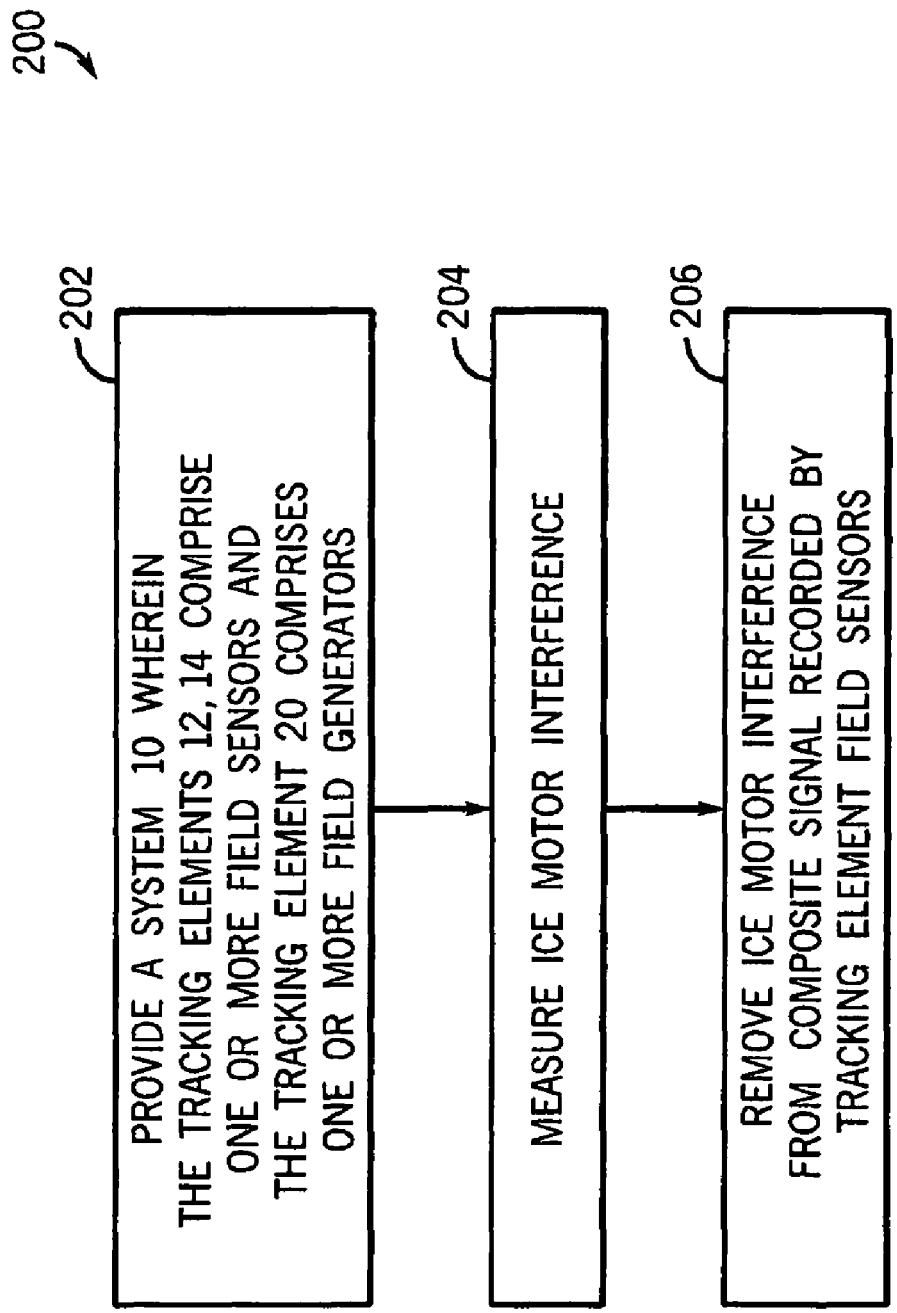
FIG. 4 is a flow chart illustrating a method in accordance with an embodiment.

Referring to FIG. 4, a block diagram illustrates a method 200 in accordance with an embodiment. The technical effect of the method 200 is to minimize tracking system interference. The individual blocks shown in FIG. 3 represent steps that may be performed in accordance with the method 200.

Referring to FIGS. 1 and 4, at step 202 of the method 200, a system 10 is provided wherein the tracking elements 12, 14 comprise one or more field sensors similar to the field sensors 13, 15, and the tracking element 20 comprises one or more field generators similar to the field generator 21. By configuring the system 10 in the manner described, the distance between the primary interference source (i.e., the ICE motor 52) and the field sensors is generally constant. Maintaining a generally constant distance between the interference source and the field sensors facilitates the process of accurately measuring and removing the interference signal as will be described in detail hereinafter.

At step 204 interference from the ICE motor 52 (shown in FIG. 2) is measured or estimated. According to one embodiment, ICE motor interference can be measured by turning off the field generators of the tracking element 20 so that the signal recorded by the field sensor of the tracking element 14 is exclusively derived from the ICE motor 52. Alternatively, the interference from the ICE motor 52 can be measured or estimated in any known manner such as, for example, by implementing ICE motor manufacturing specifications or previously acquired test data. It should be appreciated that step 204 is an optional step adapted to facilitate the process of removing the ICE motor interference at step 206.

At step 206 ICE motor interference is removed from the composite signal recorded by the field sensors of the tracking element 20. As previously described, the tracking element field sensors generally record a composite signal comprising both a tracking system signal from the field generators and a noise signal (i.e., interference) from the ICE motor 52 (shown in FIG. 2). Therefore, by removing the interference from the ICE motor 52, the remaining composite signal comprises only the tracking system signal which can be used to obtain position and orientation data with a high degree of precision.

The removal of ICE motor interference at step 206 may be performed in any known manner such as, for example, with a filter. According to one embodiment, a band-pass filter is implemented to filter out the range of frequencies produced by ICE motor interference. The band-pass filter frequency range may be selected, for example, based on ICE motor interference measurements or estimates obtained at step 204.

Referring again to FIGS. 1 and 2, another method for reducing or eliminating tracking system interference caused by the ICE motor 52 will hereinafter be described. This method implements the computer 28 to coordinate the operation of the tracking system 26 with that of the ICE motor 52. According to one embodiment, the coordination of the tracking system 26 with the ICE motor 52 includes implementing the tracking system 26 to obtain position and/or orientation data exclusively during periods wherein the motor is being operated in a manner adapted to minimize interference. The ICE motor 52 may be operated to minimize interference in a variety of manners such as, for example, completely shutting off the motor 52, reducing power to the motor 52, locking rotatable motor components (e.g., the rotor), etc. Tracking system 26 position and/or orientation data can be collected during relatively short intervals (e.g., several milliseconds) so that ICE catheter 18 operation is only minimally affected.

While the invention has been described with reference to preferred embodiments, those skilled in the art will appreciate that certain substitutions, alterations and omissions may be made to the embodiments without departing from the spirit of the invention. Accordingly, the foregoing description is meant to be exemplary only, and should not limit the scope of the invention as set forth in the following claims.

We claim:

1. A method for minimizing tracking system interference in a tracking system caused by a motor driven ultrasonic imaging device comprising:
   providing an ultrasonic imaging device adapted to obtain a generally real time three-dimensional image, said ultrasonic imaging device comprising a motor contained within a catheter housing and configured to rotate a transducer array within the catheter housing;
   estimating a noise signal produced by the motor;
   selecting a tracking system signal strength and/or frequency adapted to minimize a tracking system interference caused by the noise signal;
   implementing a field generator to produce a tracking system signal at the selected tracking system signal strength and/or frequency; and
   providing a field sensor in the catheter housing to sense the tracking system signal, wherein the field sensor is positioned away from the motor to reduce the strength of the noise signal recorded by the field sensor.

2. The method of claim 1, further comprising securing the field generator within the catheter housing.

3. The method of claim 1, wherein said estimating the noise signal comprises,:
   turning off the field generator; and
   implementing the field sensor to record the noise signal produced by the motor while the field generator is off.

4. The method of claim 1, wherein said selecting a tracking system signal strength comprises selecting a tracking system signal strength at least one thousand times greater than the strength of the estimated noise signal.

5. The method of claim 1, wherein said selecting a tracking system signal frequency comprises selecting a tracking system signal frequency at least ten times greater than the frequency of the estimated noise signal.

6. The method of claim 1, wherein said providing an ultrasonic imaging device comprises providing an intracardiac echocardiography (ICE) imaging device.

7. A method for minimizing tracking system interference in a tracking system caused by a motor driven ultrasonic imaging device comprising:
   providing an ultrasonic imaging device adapted to obtain a generally real time three-dimensional image, said ultrasonic imaging device comprising a motor contained within a catheter housing and configured to rotate a transducer array within the catheter housing;
   providing a field sensor disposed within the catheter housing such that the distance between the field sensor and the motor is generally constant;
   estimating a noise signal produced by the motor; and
   removing the noise signal from a composite signal recorded by the field sensor.

8. The method of claim 7, further comprising providing a field generator operatively associated with the field sensor.

9. The method of claim 8, wherein said estimating a noise signal comprises,:
   turning off the field generator; and implementing the field sensor to record the noise signal while the field generator is off.

10. The method of claim 7, wherein said removing the noise signal from a composite signal comprises filtering out the noise signal.

11. The method of claim 7, wherein said providing an ultrasonic imaging device comprises providing an ICE imaging device.

12. A method for minimizing tracking system interference in a tracking system caused by a motor driven ultrasonic imaging device comprising:

providing an ultrasonic imaging device adapted to obtain a generally real time three-dimensional image, said ultrasonic imaging device comprising a motor contained within a catheter housing and configured to rotate a transducer array within the catheter housing;

providing a tracking system operatively connected to the catheter housing, said the tracking system configured to estimate a position and/or orientation of the catheter housing; and coordinating the operation of the motor and the tracking system comprising:

operating the motor in a manner adapted to minimize a noise signal produced by the motor; and implementing the tracking system to estimate the position and/or orientation of the catheter housing exclusively during periods wherein said motor is being operated in a manner adapted to minimize the noise signal.

13. The method of claim 12, wherein said operating the motor in a manner adapted to minimize a noise signal includes reducing the transfer of power to the motor.

14. The method of claim 12, wherein said operating the motor in a manner adapted to minimize a noise signal includes shutting off the motor.

15. The method of claim 12, wherein said operating the motor in a manner adapted to minimize a noise signal includes locking one or more rotatable motor components.

16. The method of claim 12, wherein said providing an ultrasonic imaging device comprises providing an ICE imaging device.

* * * * *

UNITED STATES PATENT AND TRADEMARK OFFICE
CERTIFICATE OF CORRECTION

PATENT NO.         : 7,909,767 B2                            Page 1 of 1
APPLICATION NO.    : 11/866865
DATED              : March 22, 2011
INVENTOR(S)        : Li et al.

It is certified that error appears in the above-identified patent and that said Letters Patent is hereby corrected as shown below:

On Page 2, in Field (56), under "OTHER PUBLICATIONS", in Column 1, Line 3, delete "Hearth" and insert -- Heart --, therefor.

In Column 8, Line 34, in Claim 3, delete "comprises,:" and insert -- comprises: --, therefor.

In Column 8, Line 66, in Claim 9, delete "comprises,:" and insert -- comprises: --, therefor.

In Column 9, Line 17, in Claim 12, after "housing," delete "said".

Signed and Sealed this
Thirteenth Day of September, 2011

David J. Kappos
*Director of the United States Patent and Trademark Office*